United States Patent [19]
Godik

[11] Patent Number: 5,865,743
[45] Date of Patent: Feb. 2, 1999

[54] METHOD OF LIVING ORGANISM MULTIMODAL FUNCTIONAL MAPPING

[75] Inventor: Eduard E. Godik, Washington Township, N.J.

[73] Assignee: Dynamics Imaging, Inc., Mahwah, N.J.

[21] Appl. No.: 529,408

[22] Filed: Sep. 18, 1995

Related U.S. Application Data

[63] Continuation of Ser. No. 201,105, Feb. 23, 1994, abandoned.

[51] Int. Cl.$^6$ .................................................. A61B 5/05
[52] U.S. Cl. ........................................................ 600/407
[58] Field of Search ................................ 128/653.1, 664, 128/665, 633; 250/330, 341; 600/407, 473, 475, 476, 477, 310, 425, 430, 437, 438

[56] References Cited

U.S. PATENT DOCUMENTS

| | | | |
|---|---|---|---|
| 3,878,392 | 4/1975 | Yew et al. | 250/306 |
| 3,897,150 | 7/1975 | Bridges et al. | 356/5 |
| 4,207,901 | 6/1980 | Nigam | 128/660 |
| 4,212,306 | 7/1980 | Mahumud | 128/665 |
| 4,281,645 | 8/1981 | Jöbsis | 128/633 |
| 4,286,602 | 9/1981 | Guy | 128/665 |
| 4,312,357 | 1/1982 | Andersson et al. | 128/664 |
| 4,328,809 | 5/1982 | Hirschowitz et al. | 600/407 |
| 4,385,634 | 5/1983 | Bowen | 128/653 |
| 4,434,799 | 3/1984 | Taenzer | 128/660 |
| 4,495,949 | 1/1985 | Stoller | 128/664 |
| 4,515,165 | 5/1985 | Carroll | 128/664 |
| 4,536,790 | 8/1985 | Kruger et al. | 358/111 |
| 4,570,638 | 2/1986 | Stoddart et al. | 128/665 |
| 4,573,472 | 3/1986 | Ito | 128/399 |
| 4,576,173 | 3/1986 | Parker et al. | 128/633 |
| 4,583,869 | 4/1986 | Chive et al. | 374/122 |
| 4,649,275 | 3/1987 | Nelson et al. | 250/358.1 |
| 4,767,928 | 8/1988 | Nelson et al. | 250/341 |
| 4,774,961 | 10/1988 | Carr | 128/736 |
| 4,798,209 | 1/1989 | Klingenbeck et al. | 128/653 |
| 4,807,637 | 2/1989 | Bjorkholm | 128/664 |
| 4,810,875 | 3/1989 | Wyatt | 250/227 |
| 4,817,038 | 3/1989 | Knoll et al. | 364/413.24 |
| 4,817,622 | 4/1989 | Pennypacker et al. | 128/664 |
| 4,829,184 | 5/1989 | Nelson et al. | 250/358.1 |
| 4,862,894 | 9/1989 | Fujii | 128/666 |
| 4,927,244 | 5/1990 | Bahr et al. | 350/350 S |
| 4,945,239 | 7/1990 | Wist et al. | 250/358.1 |
| 4,948,974 | 8/1990 | Nelson et al. | 250/358.1 |
| 4,955,383 | 9/1990 | Faupel | 128/653 R |
| 4,995,398 | 2/1991 | Turnidge | 128/668 |
| 5,079,698 | 1/1992 | Grenier et al. | 364/413.13 |
| 5,099,848 | 3/1992 | Parker et al. | 128/661.07 |
| 5,139,025 | 8/1992 | Lewis et al. | 128/665 |
| 5,170,119 | 12/1992 | Sekihara et al. | 324/260 |
| 5,197,470 | 3/1993 | Helfer et al. | 128/634 |
| 5,213,105 | 5/1993 | Gratton et al. | 128/664 |
| 5,222,495 | 6/1993 | Clarke et al. | 128/633 |
| 5,269,325 | 12/1993 | Robinson et al. | 128/653.1 |
| 5,293,873 | 3/1994 | Fang | 128/664 |
| 5,301,681 | 4/1994 | DeBan et al. | 128/736 |
| 5,303,026 | 4/1994 | Strobl et al. | 356/318 |
| 5,305,748 | 4/1994 | Wilk | 128/653.1 |
| 5,307,807 | 5/1994 | Valdes Sosa et al. | 128/653.1 |
| 5,309,907 | 5/1994 | Fang et al. | 128/633 |
| 5,311,018 | 5/1994 | Zana et al. | 250/330 |
| 5,313,941 | 5/1994 | Braig et al. | 128/633 |
| 5,333,610 | 8/1994 | Hirao | 128/633 |
| 5,337,745 | 8/1994 | Benaron | 128/633 |
| 5,371,368 | 12/1994 | Alfano et al. | 250/341.1 |
| 5,392,210 | 2/1995 | Scholz | 364/413.01 |
| 5,402,782 | 4/1995 | Lodder | 600/407 |
| 5,515,847 | 5/1996 | Braig et al. | 128/633 |
| 5,572,996 | 11/1996 | Doiron et al. | 128/633 |

FOREIGN PATENT DOCUMENTS

| | | |
|---|---|---|
| 0099756 | 2/1984 | European Pat. Off. . |
| 0108617 | 5/1984 | European Pat. Off. . |
| 0140633 | 5/1985 | European Pat. Off. . |
| 0447708A3 | 9/1991 | European Pat. Off. . |
| 1533648 | 12/1989 | U.S.S.R. . |
| 1641268 | 4/1991 | U.S.S.R. . |
| 14032241 | 8/1975 | United Kingdom . |
| WO79/00594 | 8/1979 | WIPO . |
| WO 91/06244 | 5/1991 | WIPO . |

OTHER PUBLICATIONS de Haller EB and Depeursinge C. Simulation of time–resolved breast transillumination. *Medical & Biological Engereering & Computing* 1993; 31:165–70.*

Gandjbakche AH, Nossal R, and Bonner RF. Resolution limits for optical transillumination of abnormalities deeply embedded in tissues. *Medical Physics* 1994; 21:185–91.*

Hebden JC and Kruger, RA. Transillumination imaging performance: A time–of–flight imaging system. *Medical Physics* 1990; 17:351–6.

Levin DC, Schapiro RM, Boxt LM, Dunham L, Harrington DP, and Ergun DL. Digital subtraction angiography: principles and pitfalls of image improvement techniques. AJR 1984; 143:447–454.

Sabel M, Horst A. Recent developments in breast imaging (Review). *Physics in Medicine and Biology* 1996; 41:315–68.**

(List continued on next page.)

*Primary Examiner*—Brian Casler
*Attorney, Agent, or Firm*—Jacob N. Erlich; Jerry Cohen

[57] ABSTRACT

A method of diagnosis of a living organism by providing at least one functional map of the living organism, the method having the steps of determining at least two physical parameters characterizing the physiological state of the living organism, recording spatial-temporal distributions of the at least two physical parameters, acquiring and processing information about the spatial-temporal distributions of the at least two physical parameters, and utilizing the information about the spatial-temporal distributions of the at least two physical parameters to generate the at least one functional map of the living organism. Further steps include using one of the at least two physical parameters as a reference for selecting another of the physical parameters, substantially simultaneously recording the spatial-temporal distributions of the at least two physical parameters or recording the spatial-temporal distributions of the at least two physical parameters at a preselected time interval apart from one another.

43 Claims, No Drawings

OTHER PUBLICATIONS

Sickles EA. Breast CT scanning, heavy–ion mammography, NMR imaging, and diaphanography. In Feig SA and McLelland R eds. *Breast Carcinoma: Current Diagnosis and Treatment* 1983; New York: Masson, 233–50.

Godik, E.E., Guljaev, Yu.V., "The Human Being Through 'Eyes of Radiophysics'", *Journal of Radio Engineering* (Russian) 1991, No. 8, pp. 51–62.

Ring, E.F.J. and Hughes, H. "Real Time Video Thermography", in *Recent Developments in Medical and Physiological Imaging* a supplement to *Journal of Medical Engineering and Technology*, 1986, pp. 86–89.

Platonov, S.A., . . . , Godik, E.E., "Informative Tasks of Functional Mapping of Biological Subjects", *Journal of Radio Engineering* (Russian) 1991, No. 8, pp. 62–68.

Jacquez, J.A. et al, "Spectral Reflectance of Human Skin in the Region 235–1000 nm", *Journal of Applied Physiology*, 1955, vol. 7, No. 3, pp. 523–528.—copy not available.

"Physics of Image Visualization in Medicine", C. Webb, ed. vol. 2, pp. 241–243.—copy not available.

Krenkel, T.E., Kogan, A.G. and Tatatorian, A.M., "Personal Computers in Engineering", Izd. Mir, RiS, (Russian) 1989, p. 71.—copy not available.

Dgagupov, R.G. and Erofeev, A.A., *Piezo–Ceramic Elements in Instrument Designing and Automatics*, Leningrad, Izd. Mashinosroenie, 1986, pp. 154–155 (Russian).—copy not available.

Svechnikov S.V. "Optoelectronics elements", Moscow, Izd. Sov. Radio 1971, pp. 250–256.—copy not available.

Legett, Kate, *Optical mamography offers promise as alternative to x–ray detection*, Biophotonics International, Jan./Feb., 1996, pp. 56–57. This publication has been submitted as representative of a recent development in the field of mamography.

Godik, Eduard E. and Gulyaev, Uri, V., "Functional Imaging of the Human Body", *IEEE Engineering in Medicine and Biology*, Dec. 1991, pp. 21–29.

*Physics of image visualization in medicine*, C. Webb, ed., vol. 2, p. 382, Moscow, Mir. 1991 (Translated from English) (copy not available).

*The comparison of the sensitivity of ultrasound echo and shadow methods for determination of calcification of breast tissues*, Proc. Conf. Ultrasound Biology & Medicine—Ubiomed. VI, Warsaw–Jablonna, Sep. 19–23, 1993, pp. 41–49 (copy not available).

Ichimury, A. *Wave propagation and scattering in randomly inhomogeneous media*, vol. 1, pp. 74–79, Moscow, Mir, 1981 (Translated from English) (copy not available).

Barabanenkov, Yu. N. *On the relative increase in radiation extinction length due to correlation of weak scatterers*, USSR Academy of Sci. Proceedings, Physics of atmosphere and ocean, vol. 18, No. 7, pp. 720–726, 1982 (copy not available).

Vartapetjan, M.A. et al. *Sensor perception. An investigation experience with the help of focused ultrasound*, Leningrad, Nauka, 1985 (Russian).

*Biophysical approach to the problem of safety under the ultrasound diagnostics*, Proc. Conf. Ultrasound Biology & Medicine—Ubiomed. YI, Warsaw–Jablonna, Sep. 19–23, pp. 95–99, 1983 (copy not available).

Titce, U. and Shenck, K. *Semiconductor scheme technology*, p. 144, Moscow, Mir, 1982 (Translated from English to Russian) (copy not available).

Krenkel, T.E. et al. *Personal computers in engineering practices*, pp. 71–75, Moscow, RiS, 1989 (Russian) (copy not available).

Guljaev, Yu.V., Godik, E.E. et al. *On the possibilities of the functional diagnostics of the biological subjects via their temporal dynamics of the infrared images*, USSR Academy Nauk Proceedings/Biophysics—1984, vol. 277, pp. 1486–1491 (copy not available).

Hasset, J. *Introduction to psycho–physiology*,—Moscow, Mir, 1981 (Translated into Russian) (copy not available).

Godik, E.E., Guljaev, Yu.V. Human and animal physical fields, V mire nauki (Russian version of Scientific American)/ 1990, No. 5, pp. 74–83 (copy not available).

METHOD OF LIVING ORGANISM MULTIMODAL FUNCTIONAL MAPPING

CROSS REFERENCE TO RELATED APPLICATIONS

This application is a continuation of U.S. Patent Application Ser. No. 08/201,105 filed Feb. 23, 1994 entitled METHOD OF LIVING ORGANISM MULTIMODAL FUNCTIONAL MAPPING and now abandoned.

BACKGROUND OF THE INVENTION

The present invention belongs to the field of physics and medicine or, more precisely, to methods for characterizing and investigating the functional state of living organisms and the functional dynamics of the physiological processes taking place during the living organism's vital activity.

Living organism functional mapping reveals the earliest signs of pathologies on the basis of the integral picture of the organism's functioning. This opens up the possibility of avoiding radical methods of treatment which become necessary when such pathologies are revealed at a later stage of their development. That is why the methods related to the living organism's early functional diagnostics are very promising for the population screening and for development of preventive medicine.

For a long time, functional diagnostics of a living organism's state was performed only with the use of various tests which determined the quality and/or the reaction rates of the organism's physiological systems. Such tests made it possible to only estimate the functional state of the living organism's system when the organism was involved in some purposeful activity. Since the overall picture of the organism functioning was not investigated, such measurements did not give rise to the possibility of performing early diagnosis of pathology.

Only lately, when modern radio physics (electromagnetic theory) methods were applied to biomedical research, the possibility appeared of recording a complex picture of the spatial-temporal dynamics of a living organism's physical fields and radiations, yielding important information on the state of the organism's various regulative systems and organs in the course of natural vital activity.

The human body or organism is a dynamic self-regulative system. Its stability (homeostasis) is provided by the continuous functioning of different physiological systems. Variations in the organism's physiological parameters result in changes of the biological tissue's physical parameters, such as, for example, the temperature, dielectric permeability, magnetic susceptibility, electric impedance and potentials, currents, etc. The organism's functional dynamics are reflected in the above mentioned dynamic distributions of its physical parameters. Information on the functional dynamics are revealed in the real time scale by the dynamics of the organism's physical fields and radiations: infrared (IR), microwave, acoustical, optical radiations, electric and magnetic fields. Under these conditions, external fields and radiations become parmetrically modulated, with those of natural origin such as geomagnetic, electric, light, etc., being first observed.

Different methods of investigating and diagnosing a living organism's state which employ recording the above mentioned physical parameters are known.

For example, to determine the biological tissues' temperature, the tissue's own electromagnetic thermal radiations, which are most intensive at the middle IR-wavelength range, are recorded. Infrared dynamic thermal mapping methods, as described in Guljaev, Yu V., Godik, E. E. et al.,"on the possibilities of the functional diagnostics of the biological subjects via their temporal dynamics of the infrared images," USSR Academy Nauk Proceedings/Biophysics, 1984, vol. 277, pp. 1486–1491, are based on such measurements. This method permits both measuring the tissue temperature with accuracy better than 0.1 degree and investigating the spatial-temporal distribution of blood microcirculation at the near surface tissues of the living organism. To accomplish this, temporal changes in the spatial distribution of IR-thermal radiation intensity of the living organism tissues are recorded, which provides the spatial-temporal microcirculation dynamics in these tissues. This method is used for investigation of both the spontaneous functional dynamics and functional dynamics initiated by the reactions of the physiological systems to different functional tests: reflective and humoral ones. The data thus obtained are represented in the form of the temporal sequences of the thermal images and/or the spatial-temporal cuts. Pain reactions, hyper- and hypo- ventilation and the effects of pharmaceutical treatments are able to be visualized under these conditions. In addition, this method reveals regions with various disturbances in the regulative mechanisms, and differential diagnostics of such disturbances can be performed. This method also permits estimating the state of the internal organs via the study of the spatial-temporal dynamics of the IR-radiation intensity recorded at the areas where the dermatomers reflectively connected with the corresponding organs are located.

However, the main disadvantage of the above described method is that it does not permit investigating the functional interconnection between various physiological processes which occur in a living organism under investigation. IR-thermal radiation provides information only about the dynamics of slow microcirculation, since the depth examined does not exceed 100 um. At the same time, the process of the thermal projection to the skin surface of the deeper layers of the blood flow network takes several seconds. For this reason, the above method does not permit investigating the fast blood flow dynamics connected, for example, with cardio and/or respiratory processes. The application of this method for the description of the living organism's functional state is restricted by information contained in the slow temporal dynamics of the skin surface temperature.

Another well known method of living organism functional diagnostics is a multichannel measurement of physiological parameters. A whole family of the well known methods of multichannel polygraphy is based on such approach, as described in Hasset, J,"Introduction into psycho-physiology," Moscow, Mir, 1981 (translated into Russian), for example. According to this method signals or information derived simultaneously from several channels are measured. The most complete set of information is represented by simultaneous measurements of the electroencephalogram, electrocardiogram, arterial pressure, skin electric resistance and/or skin galvanic reaction, skin temperature, plethysmogram and electromyogram, as described in, for example, Yoshihiro, Ito, "Autogenic training and treating apparatus," U.S. Pat. No. 4,573,472, 4 Mar. 1984. On the basis of the temporal dynamics of the recorded parameters, the living organism's functional state is judged. Recording of several different physiological signals gives a more accurate description of the organism's state.

At the same time, the multichannel polygraphy method reflects the temporal dynamics of the above parameters only at several discrete points of the organism and neither permits determination of the spatial distribution of the physiological reactions, i.e., the spatial portrait of the living organism's functioning, nor the investigation of the functional dynamics of the whole-organism's connectivity of the physiological systems.

A method of functional diagnostics based on multichannel mapping of the spatial-temporal distributions of the physical field tensions and radiation intensities of the human body (living organism) is also known, and described in Godik, E. E., Guljaev, Yu V. Human and animal physical fields, "V mire nauki" (Russian version of Scientific American), 1990, no. 5, pp. 74–83. This method is based on the following approach to determining the functional state of a living organism.

The human body or living organism, as a self-regulative system, is functionally inhomogenous and non-stationary. For that reason its functioning and its multilevel regulative mechanisms are described by a hierarchy of rate constants from milliseconds to minutes, hours to days, etc. An adequate method of providing radio physical (electromagnetic) monitoring of such a system is called dynamic mapping, i.e., recording the temporal sequences of the instantaneous distributions (maps) of the physical fields tensions and/or radiation intensities over time intervals which are much less than the corresponding time constants of the regulative processes. The temporal map sequences thus obtained are called dynamic maps.

For example, to determine the tissue temperature of a living organism, its electromagnetic thermal radiation is recorded by means of infrared dynamic thermovision. The details of this method were described above.

More specifically, a low intensity microwave thermal radiation comes from the organism's depth. Its brightness reflects non-inertially the functional dynamics of heat production and blood flow rate in the muscles, brain cortex and internal organs. Recording of such radiation is performed at wavelengths of about 3–30 cm, while the depth it comes from is of the order of 2–5 cm.

More detailed information about the spatial distribution of the thermal production functional dynamics inside the living organism is revealed by thermal acoustic radiation at an ultrasound frequency range of hundreds kilohertz to megahertz (corresponding to a wavelength of about 1 mm). Ultrasound waves, produced by thermal acoustic noise of the organism's tissues, come to the organism's surface from a greater depth (5–10 cm) and bring information, in real time scale, about functioning of the internal organs, such as the liver.

The organism's fast reflective regulation and functioning are revealed, in particular, in neural activity and in the muscular excitation processes. Information on these fast processes (the characteristic times are in the millisecond region) is revealed by a dynamic picture of the electrical potentials at the skin surface, and, especially, by the spatial-temporal dynamics of the magnetic fields around the body surface. Electric activity of the living organism's heart and brain are investigated by means of magnetic dynamic mapping.

Without illumination, extra weak radiation (chemoluminescence) of the skin covers connected with lipid peroxidation is observed in the optical yellow-green spectral range. Its intensity is determined by the antioxidizing status of the organism investigated. Under conditions of external illumination, the chemiluminescence intensity increases and, in addition, temporally and spectrally dynamic optical pictures appear at the near 1R-wavelength range. It is the radiation back scattered by the biological tissues that produces this picture; it comes from the depth of up to one centimeter and characterizes the functional redistribution of the physiological pigments, especially various forms of blood hemoglobin.

In addition to the living organism's own physical fields and radiations, the organism's functional status is reflected in the external fields and radiations spatial-temporal dynamics, which are modulated as a result of the living organisms' physiological system's activity. Thus, blood redistribution related to cardiac pulsations is parametrically reflected in the geomagnetic field spatial-temporal dynamics near the torso, and the microcirculation dynamics of the capillary blood content is parametrically reflected by means of changes in the electrical tissue impedance. Electrical tissue impedance is measured by means of spatial-temporal distribution of external electrical fields having frequencies from tens to hundreds of kilohertz.

A considerable disadvantage of this latter method is that the dynamic maps provided by the measured parameters are considered separately. Furthermore, this method does not permit a comparison of variations in the spatial and temporal dynamics in different physical parameters which provide information on the state of different physiological systems and processes. In addition, this disadvantage relates equally to all the above described methods and noticeably limits their potential to reveal pathology.

Let's consider, for example, muscle functioning. Approximately a second before a mechanical contraction of a muscle takes place, a source of an electric excitation appears at the motor brain cortex. This excitation is reflected within the millisecond time interval in the dynamic maps of the electrical potential at the scalp and in those of the magnetic field around the head. Then, the dynamic picture of the electric and magnetic signals at the immediate proximity of the muscle surface develops, reflecting electric motor neuron excitation. Further, the whole muscle is affected by this electric excitation and this latter process is reflected in the delayed dynamics of the skin electric potential and magnetic field above the muscle. All these processes proceed in about one second, and only after their completion does a mechanical muscle contraction develop. In tens of seconds after this, radio thermal and acoustico thermal radiations are increased, characterizing the "energy payment" for the muscle contraction. An increase in the microcirculation, supporting the muscle tissue metabolic resource, is reflected in the multispectral dynamic map of the back scattered optical radiation of the near IR-range, and also in the dynamic map of the muscle tissue electric impedance.

Consequently, the most complete information on the functional state of a physiological system and organ could only be obtained via the simultaneous measurements of a set of independent parameters of physical fields and radiations measured at different spectral ranges. None of the existing methods permit the analysis of the spatial-temporal interconnection between the dynamic maps recorded for different ranges. It is the interconnection of the above mentioned parameters that reflects the functional connectivity of any organ within the living organism. Pathology at an early stage is revealed in the disturbances of such connectivity.

SUMMARY OF THE INVENTION

The main object of the present invention provides a method of functional mapping of a living organism to permit the interconnection of characteristics of the spatial-temporal dynamics of at least two parameters of the physical fields and radiations in order to diagnose the investigated organism on the basis of the integral picture of the physiological processes' functional connectivity.

The method of this invention directed to recording the spatial-temporal distribution of at least one physical parameter, characterizing the physiological state of the living organism diagnosed. To determine the characteristics of the spatial-temporal distributions for each of the physical parameters, comparison is made with the characteristics recorded for the same living organism but at a different spatial area or at different time interval, or with similar characteristics obtained for another living organism. The results of such a comparison determine the functional state of the living organism diagnosed. In accordance with the invention, the spatial-temporal distribution of at least one physical parameter of the living organism diagnosed is recorded, and at least one interconnection characteristic of the spatial-temporal distributions of the recorded physical parameters is determined. The characteristics obtained are then compared with similar interconnection characteristics recorded for the same organism at different spatial or temporal ranges, or with similar characteristics of the same physical parameter recorded for another living organism. The results of such a comparison determine the functional state of the diagnosed living organism.

The above described procedure makes it possible to diagnose a living organism's state on the basis of an integral picture of the functional connectivity of physiological processes.

It is expedient to record the spatial-temporal distributions of both a living organism's own physical field's tensions and radiation intensities as well as physical characteristics of its surface and external fields' tensions and/or intensities of external radiations, which are modulated due to the presence of another living organism. It is expedient, under these conditions, to record at least two such physical parameters simultaneously. Recording at least two parameters permits using the spatial-temporal dynamic characteristics of one of the physical parameters recorded for choosing the parameters for the other parameter recording: the beginning and the frequency of measurements and the necessary data volume. This helps to reduce the volume of the data analyzed and to simplify the means and equipment for the data accumulation. One parameter from the two simultaneously recorded parameters is used for synchronous accumulation and detection of the other parameter; this is especially useful for the non-invasive measurements of the above physical parameters under the conditions of low signal/noise ratio and at the presence of background disturbances.

It is expedient to divide the spatial-temporal distributions of each of the recorded physical parameters into the regions functionally connected with each other. This procedure permits the determination of the interconnection characteristics of the spatial-temporal distributions of these parameters. The interconnection characteristics provide information on the functioning of the diagnosed living organism's physiological systems and organs.

The elements of the integral spatial-temporal distribution of the recorded physical parameters could be used for investigation of the cross-correlation characteristics of the physiological processes for performing the analysis of their temporal delays and time scales, for revealing their spatial inhomogeneities and for obtaining other important data pertinent to the living organism functional diagnostics method.

DETAILED DESCRIPTION OF THE PREFERRED EMBODIMENT

The method of the present invention involves recording the spatial-temporal distributions of one or several parameters (dynamic maps) of physical fields and radiations, providing information about physiological processes at (or near) the surface of the diagnosed living organism. Either simultaneously or after some time interval, the spatial-temporal distributions of one or several other parameters of the physical fields and radiations also at (or near) the same living organism's surface are measured.

The recorded parameters or measurements are the living organism's own physical fields' tensions and/or radiation intensities, as well as external fields' tensions and/or external radiations intensities changed as a result of the presence of the living organism investigated. Alternatively, the physical characteristics of another living organism's surface can be measured and combined with the above measurements. The first or higher order time and space derivatives of the physical parameters are often also recorded.

These spatial-temporal distributions of the physical parameters are called dynamic or functional maps.

The physical parameters depicted by the dynamic map by itself and, especially, the interconnection characteristics of the spatial-temporal dynamics parameters contain information on the functioning of the living organism's physiological systems. In order to determine the functional status of the living organism, the characteristics of the interconnection between several physical parameters are analyzed. In the simplest case, only two parameters are considered.

Of special importance while constructing the aforementioned functional or dynamic maps, is the analysis of the parameters' temporal behavior. Such analysis is performed by the comparison of the information elements of the parameters' dynamic maps, representing temporal behavior of the parameter at some spatial point or that averaged over some spatial area of the dynamic map. Sometimes, it is more convenient to use, as the information element of the parameter's dynamic map, a temporal regularity in the behavior of the histogram of the parameter amplitude at some fixed value of the latter. In particular, it is expedient to choose the parameters recorded so that they characterize different time scales in the living organism functional activity.

The analysis of the interconnection between the parameters dynamic maps makes it possible to reveal essential features of the whole-organism's spatial-temporal dynamics reflecting functional connectivity of the living organism's physiological processes which are responsible for the parameters recorded. The calculated interconnection characteristics give the quantitative estimations of these features.

The interconnection characteristics of the parameters' dynamic maps describe the temporal interconnection, the characteristic times, the mutual delays and the frequencies of the living organism's physiological processes. They permit determining the size and the characteristic scales of the physiological processes and, thereby, open up the possibility of the most complete description of the functional state of the living organism.

In order to perform the functional diagnosis of a living organism, dynamic maps of the physical parameters, as well as the corresponding interconnection characteristics, are obtained and are compared with similar dynamic maps of the parameters and their interconnection characteristics obtained from the same organism at another spatial area or for another time interval, or with those obtained for another living organism. With the results obtained from such a comparison, the functional state of the living organism is determined.

The interconnection characteristics of the physical parameters' dynamic maps permit an unambiguous determination of the functional state of the living organism at different time periods, even if some separate dynamic maps of the recorded parameters are coincident. The method of this invention for providing a functional diagnostics of a living organism's state makes it possible to determine both the functional status of the whole-organism's physiological systems and some of the separate systems and organs of the living organism investigated.

Examples of the most informative combinations of the recorded physical parameters are the following dynamic map combinations:

electric potential of the living organism's surface and the intensity of the microwave thermal radiation and/or the intensity of the acoustic radiation and/or infrared radiation intensity, or the tension of magnetic field near the living organism's surface and the intensity of the microwave thermal radiation and/or the intensity of the acoustic radiation and/or electric potential of the living organism's surface, or the coefficients of the optical radiation back scattered by the investigated area of the living organism and/or of that transmitted through this area, measured simultaneously at least at two wavelengths, and/or the intensity of the infrared radiation, or the intensities of the infrared and/or acoustic radiations and/or microwave thermal radiation of the living organism and/or one of the parameters of the spectral dependence of the coefficients of the back scattered and/or of the transmitted optical radiation.

The functional maps obtained are used for the formation of the characteristic images of the functional layers of the living organism differing by their depth: the skin, muscles, temperature core, etc. By means of the analysis of the characteristic images of these functional layers and taking into consideration the picture of the spatial-temporal distribution of the organism's functioning, the organism's functional status is determined. The characteristics of the spatial-temporal distribution of the functioning thus obtained are used as the feedback parameters when the living organism is the subject to the influcence of some external sensor.

With the purpose of a comparative analysis of the parameters' dynamic maps, especially when the calculation of their interconnection characteristics is performed, some elements of the initial information and a set of specific features for each of such elements are applied. To calculate the interconnection characteristics, some digital measurements of the features proximity are used. The information elements could be chosen independently for each of such maps under these conditions, or they could be chosen and constructed using the whole aggregate of the dynamic maps under the consideration.

The dynamic maps of several physical parameters are recorded simultaneously or with a time delay. The time delay being determined by the type of the physiological process investigated, the method of activation of these processes and by the physical characteristics of the tissues and organs of the living organism.

To activate physiological processes during the process of living organism functional diagnostics, some sensor influences and/or functional exercises are applied. For example, such influences include external temperature changes, changes in humidity, application of illumination, sound, mechanical influences, electric stimulation, alternating magnetic field or pharmacologic treatments. Functional exercises include some purposeful behavior of the living organism, for instance, muscle strain, hypo- and/or hyperventilation, intellectual loading, etc.

When at least two parameters are measured during the method of this invention in which simultaneous dynamic maps are recorded, one of the parameters could be used as a reference for the other. The features of the information elements of this reference parameter dynamic map are used, in real time or in a subsequent data treatment, for a synchronous and/or a pseudo-synchronous detection and data accumulation under conditions when periodical physiological processes are investigated. The reference parameter's features are used for a choice of the other parameter's recording regime and, in particular, for determination of the spatial scale and/or time frequency of the process of recording the dynamic maps for these latter parameters. Thereby, the conditions of the spatial-temporal continuity of the dynamic maps recorded for the investigated physiological process are obtained. The reference parameter features are used also for determination of the time intervals and spatial regions while recording the other parameters, thus permitting considerable reduction of the volume of the information processed.

As an information element of the dynamic map of the reference parameter, the parameter's temporal behavior at some spatial point, or averaged over some spatial region of the dynamic map, is used.

Sometimes, it is more convenient to use a two-dimensional spatial distribution of the reference parameter at some definite moment or averaged over some period of time.

Functional diagnosis of the living organism's state based upon dynamic maps of the recorded parameters presumes determination of changes in the spatial areas, characteristic times and definite regularities in the recorded parameters in relation with one or another physiological process.

Recording of several parameters makes it possible to analyze the interconnection between the dynamic maps obtained for different parts of the living organism body, reflecting different stages in the development of the functional dynamics of the physiological processes. Such an analysis makes it possible to reveal the character of the functional connectivity both between different physiological systems (and/or organs) and inside them. In particular, the data obtained permits determination of the functional manifestations of different steps in the development of the physiological processes inside separate regions of the living organism.

Based upon the above, the dynamic maps of two or more parameters are divided into the areas functionally connected with each other. The dynamic maps of the first parameter are used for the clustering of the other parameter's dynamic maps and for the construction of the corresponding functional maps and vice versa. The functional maps of the parameters represent by itself functional images containing several clusters, each characterizing certain functional behavior The analysis of these functional maps for the living organism under diagnosis and the calculation, on the basis of such maps, of the characteristics of the functional interconnection between the physiological systems and processes yield information regarding the living organism's functional status.

Sometimes, the most important information about the functional connectivity is revealed by the rates of the parameter's temporal and/or spatial changes. Corresponding parameter derivatives determined by their dynamic maps serve as the information elements in such a case.

The analysis of the correlation between the information elements chosen and their features is performed for several parameters. In particular, functional maps are constructed reflecting the degree of the physiological processes manifestation, their rates and/or time delays. When it is necessary to analyze the synchronous functioning of different parts of the living organism, the parameter's functional maps are constructed on the basis of the cross-correlation between the selected elements of the parameter's dynamic maps. Of considerable interest for the analysis of the functional connectivity is the construction of the functional maps reflecting the qualitative similarity in the parameter's temporal behavior. This implies the construction of the areas with qualitatively similar dynamics, for example, the areas where an increase or a decrease (or some variation of such behavior) in the parameter's amplitude takes place.

For a more detailed description of the functional connectivity, the information elements of the dynamic maps of some parameters are expressed as a function of the information elements of the dynamic maps of the other parameters. The other method for functional map construction is decomposition of the information elements of some parameter's dynamic maps over some basis constructed by the information elements of the other parameter's dynamic maps. In particular, quite informative are the functional maps constructed with the use of the separation of the functional areas which are determined by a small number of factors connected with the physiological processes investigated.

To investigate the temporal-spatial distribution of the functions, spatial-temporal projections are created representing temporal distributions of the parameter's spatial changes over some chosen direction. This results in two-dimensional cuts of the parameters' dynamic maps being used as the information elements.

Spatial distribution of the functioning in the form of the corresponding functional maps is investigated by the analysis of the interconnection between the features of the information elements or some functions of these features. The construction of the functional (dynamic) maps presumes that the values of the features lie at some definite interval and that some logical terms are satisfied. The functional maps thus obtained contain information about the spatial scales of the physiological processes' functional manifestations of a similar type, about the presence of similar spatial shifts of the areas with maximal manifestation of the organism physiological processes, and about the waves and the spatial peculiarities in the functional dynamics.

To improve the reliability of the functional diagnosis of the living organism's state, the analysis of the functional connectivity of different physiological systems and organs is performed. Such an analysis permits analyzing the degree of the living organism's functional homogeneity under different conditions. For instance, changes in the spectral characteristics of the muscle's microtremor under the stress conditions are well known. Also, changes in correlation of the electric rhythms of the internal electric current generators are known to take place at different functional disturbances, etc. The method of this invention of living organism functional diagnostics makes it possible to reveal the absence or presence of the functional interconnection, to estimate the degree of this interconnection, to reveal the concealed interconnections between physiological processes, and to unravel the regularities in the functioning of the organism, on the basis of the integral spatial-temporal dynamics of the parameters recorded.

The analysis of the integral spatial-temporal dynamics of the parameters reveals the areas in the dynamic (functional) maps which are characterized by belonging to some definite class of the integral functional behaviors. Under these conditions, the main role is played not only by the similarity in the temporal dynamics or in the spatial distribution of the parameters in comparison with each other, as it was described above, but also by the interconnection of the parameter's spatial-temporal dynamics with some characteristics of the physiological processes. To obtain the clustering of the parameters' dynamic maps into different functional areas and to construct the functional maps, the characteristics of the spatial-temporal dynamics of the physiological processes used are obtained on the basis of some model description of the physiological processes.

In order to reveal the integral spatial dynamics at different areas of the living organism, the spatial distribution of the organism's functioning is analyzed. In this case, as information elements, integral spatial dynamics of changes in the value of the parameters along some chosen directions, or integral two-dimensional spatial distributions of the parameters at some fixed moment or that averaged over some time interval, or integral two-dimensional spatial-temporal distributions of the parameters at fixed values of one spatial coordinate or that averaged over some interval of changes in some of the spatial coordinates are chosen.

The compared features of the integral information elements utilized in the construction of the functional maps are the characteristics of the element amplitude, its spatial or temporal frequency or phase. Often the correlation between the features is analyzed by means of calculation of the pair cross-correlation coefficients. In more complicated cases, numerical measures of the qualitative similarity of the features of the integral elements are used, in order to compare the qualitative character of the integral dynamics of the parameters under consideration.

In the most complicated cases, a matrix of the paired distances of the features for all of the information elements under consideration and for all the dynamic maps of the recorded parameters are elaborated upon. On the basis of such a matrix, a set of the functional maps is. constructed reflecting various aspects of the integral spatial-temporal dynamics of the parameters. It is possible, for example, to construct the hierarchy of the divisions into the functional areas relying upon the degree of the homeogenity in the functioning of the living organism investigated areas.

Sometimes, together with or instead of the spatial-temporal distributions of the organism's own physical parameters, similar distributions of an external sensor are recorded. Under these conditions, the characteristics of the integral spatial-temporal behavior of the recorded parameters are considered while performing the functional diagnostics.

I claim:

1. A method of diagnosis of a living organism by providing at least one functional map of the living organism, the method comprising the steps of:

determining at least two physical parameters characterizing a physiological state of said living organism;

recording spatial-temporal distributions of said at least two physical parameters;

acquiring and processing information about said spatial-temporal distributions of said at least two physical parameters;

generating from said information about said spatial-temporal distributions of said at least two physical parameters said at least one functional map of the living organism; and diagnosing the living organism by analyzing said at least one functional map of the living organism.

2. The method as defined in claim 1 further comprising the step of using one of said at least two physical parameters as a reference for selecting another of said physical parameters.

3. The method as defined in claim 1 further comprising the step of substantially simultaneously recording said spatial-temporal distributions of said at least two physical parameters.

4. The method as defined in claim 1 further comprising the step of recording said spatial-temporal distributions of said at least two physical parameters at a preselected time interval apart from one another.

5. The method as defined in claim 1 further comprising the step of analyzing interconnection characteristics between said spatial-temporal distributions of said at least two physical parameters in order to determine functional status information of the living organism.

6. The method as defined in claim 5 further comprising the step of generating from said determined information said at least one functional map of the living organism based upon said interconnection characteristics between said spatial-temporal distributions of said at least two physical parameters.

7. The method as defined in claim 6 further comprising the step of analyzing said interconnection characteristics between said spatial-temporal distributions of said at least two physical parameters taken from different parts of the living organism.

8. The method as defined in claim 6 further comprising the step of analyzing said interconnection characteristics between said spatial-temporal distributions of said at least two physical parameters taken from the surface and deep layers of the living organism.

9. The method of claim 5 further comprising the steps of determining a plurality of physical parameters and selecting said physical parameters over time during the living organism's functional activity.

10. The method as defined in claim 5 further comprising the steps of obtaining at least one functional map and interconnection characteristics of another living organism, and comparing said at least one functional map and interconnection characteristics of said living organism with said at least one functional map and interconnection characteristics of said another living organism, wherein the comparison thereof provides additional information on said functional status of said living organism.

11. The method of claim 1 further comprising the steps of determining a plurality of physical parameters and selecting said physical parameters over time during the living organism's functional activity.

12. The method of claim 11 wherein at least one of said physical parameters are determined based upon the living organism's own physical fields.

13. The method of claim 11 wherein at least one of said plurality of physical parameters is related to electrical potential of the living organism's surface.

14. The method of claim 11 wherein at least one of said plurality of physical parameters is related to magnetic fields near the living organism's surface.

15. The method of claim 11 wherein at least one of said plurality of physical parameters is related to optical radiation in a visible range at least at one wavelength backscattered from an area under investigation of the living organism.

16. The method of claim 11 wherein at least one of said physical parameters are determined based upon the living organism's own radiation.

17. The method of claim 11 wherein at least one of said physical parameters are determined as a result of external physical fields applied to the living organism.

18. The method of claim 11 wherein at least one of said physical parameters are determined as a result of external radiation applied to the living organism.

19. The method of claim 11 wherein at least one of said plurality of physical parameters is related to electrical potential of the living organism's surface and intensity of microwave thermal radiation of the living organism.

20. The method of claim 11 wherein at least one of said plurality of physical parameters is related to electrical potential of the living organism's surface and the intensity of acoustic thermal radiation of the living organism.

21. The method of claim 11 wherein at least one of said plurality of physical parameters is related to electrical potential of the living organism's surface and the intensity of infrared thermal radiation of the living organism.

22. The method of claim 11 wherein at least one of said plurality of physical parameters is related to electric potential of the living organism's surface.

23. The method of claim 11 wherein at least one of said plurality of physical parameters is related to intensity of microwave thermal radiation of the living organism.

24. The method of claim 11 wherein at least one of said plurality of physical parameters is related to acoustic thermal radiation of the living organism.

25. The method of claim 11 wherein at least one of said plurality of physical parameters is related to infrared thermal radiation of the living organism of the living organism.

26. The method of claim 11 wherein at least one of said plurality of physical parameters is related to optical radiation in a near infrared range at least at one wavelength backscattered from an area under investigation of the living organism.

27. The method of claim 11 wherein at least one of said plurality of physical parameters is related to optical radiation transmitted through an area under investigation measured substantially simultaneously with intensity of infrared thermal radiation of the living organism.

28. The method of claim 11 wherein at least one of said plurality of physical parameters is related to the optical radiation transmitted through an area under investigation measured substantially simultaneously with the intensity of acoustic thermal radiation of the living organism.

29. The method of claim 11 wherein at least one of said plurality of physical parameters is related radiation transmitted through an area under investigation measured substantially simultaneously with an intensity of microwave thermal radiation of the living organism.

30. The method as defined in claim 1 further comprising the step of applying at least one external influence to said living organism; wherein the diagnosis takes place during the application of said at least one external influence to said living organism.

31. The method as defined in claim 30 wherein at least one of said external influences comes from changes in temperature.

32. The method as defined in claim 30 wherein at least one of said external influences comes from changes in humidity.

33. The method as defined in claim 30 wherein at least one of said external influences comes from an application of illumination.

34. The method as defined in claim 30 wherein at least one of said external influences comes from an application of sound.

35. The method as defined in claim 30 wherein at least one of said external influences comes from an application of mechanical influence.

36. The method as defined in claim 35 wherein said mechanical influence includes an application of external pressure.

37. The method as defined in claim 30 wherein at least one of said external influences comes from an application of electric stimulation.

38. The method as defined in claim 30 wherein at least one of said external influences comes from an application of magnetic stimulation.

39. The method as defined in claim 30 wherein at least one of said external influences comes from a pharmacological treatment.

40. The method as defined in claim 30 wherein at least one of said external influences comes from exercise.

41. The method of claim 1 wherein said at least one functional map contains several components, each of said components characterizing certain functional behavior characteristics of the living organism.

42. The method of claim 41 wherein different parts of the living organism are diagnosed by the step of cross-correlating several of said components of said at least one functional map.

43. The method as defined in claim 1 further comprising the step of determining the derivative of said physical parameters and using a spatial-temporal distribution of said derivatives to generate said at least one functional map of the living organism.

* * * * *